United States Patent [19]

Cannon

[11] Patent Number: 5,123,838
[45] Date of Patent: Jun. 23, 1992

[54] ORTHODONTIC BRACKET

[76] Inventor: James L. Cannon, 1225 Sherwood Park Dr., Gainesville, Ga. 30501

[21] Appl. No.: 626,760

[22] Filed: Dec. 13, 1990

[51] Int. Cl.⁵ .................................................. A61C 3/00
[52] U.S. Cl. ...................................................... 433/14
[58] Field of Search ................... 433/8, 9, 10, 14, 16, 433/17

[56] References Cited

U.S. PATENT DOCUMENTS

| | | | |
|---|---|---|---|
| 1,821,171 | 9/1931 | Atkinson | 433/14 |
| 2,125,587 | 8/1938 | Richardson | 433/14 |
| 2,196,516 | 4/1940 | Atkinson | 433/14 X |
| 2,686,365 | 8/1954 | Schurter | 433/14 |
| 3,134,171 | 5/1964 | Kessler | 433/14 |
| 3,163,933 | 1/1965 | Begg et al. | 32/14 |
| 3,178,821 | 4/1965 | Kesling | 32/14 |
| 3,178,822 | 4/1965 | Fogel et al. | 32/14 |
| 4,427,381 | 1/1984 | Hall | 433/14 |
| 4,443,189 | 4/1984 | Wildman | 433/10 |
| 4,573,913 | 3/1986 | Creekmore | 433/17 |
| 4,669,980 | 6/1987 | Degnan | 433/17 X |
| 4,838,787 | 6/1989 | Lerner | 433/14 |
| 4,917,602 | 4/1990 | Broussard | 433/8 |
| 4,941,825 | 7/1990 | Lerner | 433/14 |
| 5,037,287 | 8/1991 | Lerner | 433/14 |

OTHER PUBLICATIONS

60860, Type 316L Stainless Steel Shot Form. Techniques and treatment, pp. 720-723, 725.
ES121001, Styrene-low density, GP Grade.
ES12003, Styrene-low density, GP Grade.

Primary Examiner—Robert P. Swiatke
Assistant Examiner—Nicholas D. Lucchesi
Attorney, Agent, or Firm—Jones, Askew & Lunsford

[57] ABSTRACT

There is disclosed an improved orthodontic bracket comprising a body member having a base surface, a top surface and two opposing side surfaces; slots formed in the top surface having a depth substantially equal to the position of the slot in the side surface so that when archwires are received in the slots and retained in the slots by a retaining member both archwires will be positioned the same distance from the base surface thereby providing both archwires with the same in/out compensation.

5 Claims, 4 Drawing Sheets

ORTHODONTIC BRACKET

FIELD OF INVENTION

The present invention relates generally to an improved orthodontic bracket, and, more specifically, to a combination orthodontic bracket for use in the application of both the edgewise technique and the lightwire technique which bracket provides the same "in/out" compensation for both the edgewise and lightwire archwire slots. The improved orthodontic bracket of the present invention also includes an improved system for attaching and retaining simultaneously an edgewise archwire and a lightwire archwire to the bracket.

BACKGROUND OF THE INVENTION

Orthodontic brackets which are applied to teeth, either by attachment to a band or by direct bonding to a tooth, for the purpose of applying a moving force to the tooth to which the bracket is attached are known in the art. The moving force is generated by a wire attached to the orthodontic bracket which wire is also attached to similar brackets attached to adjoining teeth. The moving force applied to teeth over a period of time permits the movement of the teeth to accomplish desired alignment of the teeth.

There are basically two techniques for applying this moving force currently in practice in the orthodontic field. The conventional edgewise technique of applying this moving force is characterized by the use of a bracket having a rectangularly sectioned archwire receiving slot (edgewise slot). The moving force in this type of bracket (edgewise bracket) is applied to the tooth by the application of an angular torque from a mating edgewise archwire. The archwire is captured in the edgewise slot by a relatively small gauge stainless steel tie wire or by a small donut-shaped retaining member made from a resilient rubber-like material.

The edgewise bracket is typically used for bodily movement of teeth. To accomplish this movement more expeditiously, edgewise brackets are often designed to induce a predetermined type of force. These predetermined forces include, for example, a torque force to adjust a tooth with respect to its labio-lingual inclination or an angulation force to adjust the mesio-distal positioning of individual teeth. Brackets which have these predetermined forces built into their design are said to be pretorqued and preangulated. Pretorqued and preangulated edgewise brackets reduce the need for time and labor intensive archwire adjustments.

Another built-in design feature of prior art edgewise brackets is "in/out" compensation. This type of compensation is necessary due to variation in crown facial prominence; that is, the distance from the embrasure line to each crown's most prominent facial point. Average maxillary crown prominence ranges from approximately 2.9 mm for first and second maxillary molars to 1.65 mm for maxillary lateral incisors and from 2.5 for mandibular molars to 1.2 mm for mandibular incisors. When an archwire is applied to a series of edgewise brackets without in/out compensation, a smooth curve of the archwire will not meet all of the edgewise brackets. Therefore, a series of complicated bends must be made in the archwire in order to properly engage each edgewise slot. The bending of an archwire to fit the in/out of a particular patient's teeth requires a significant amount of time and effort. Accordingly, edgewise brackets have been made with built-in in/out compensation provided by edgewise brackets having various base thicknesses. The variable base thicknesses adjust the distance of the edgewise slot from the tooth surface and thereby place the edgewise slot of the edgewise bracket in alignment with adjacent edgewise brackets so that an archwire having a smooth curved shape can be attached to each bracket.

The other orthodontic technique which is presently used is known as the Begg lightwire technique. This technique involves the use of a relatively light, round sectioned archwire. A lighwire bracket typically includes a mesio-distally extending slot for receiving the archwire. The archwire is captured and secured in the lightwire slot by a pin having an elongate body portion and an enlarged head portion. The pin is inserted into a slot in the body of the lightwire bracket which thereby captures the archwire between the head of the pin and the body of the bracket. The pin is then secured to the lightwire bracket by bending the elongate portion of the pin over the body of the bracket. An example of a lighwire bracket is shown in U.S. Pat. No. 3,178,821.

The archwire slot of the lightwire bracket and the pin method of attaching an archwire thereto permits free tipping of the teeth (either labio-lingually or angularly). The lightwire brackets of the prior art have not been known to include pretorque, preangulation or proper in/out compensation.

Both the edgewise technique and the lightwire technique have advantages under different circumstances. Furthermore, both techniques may be used at different times on the same patient or in conjunction with each other at the same time on the same patient. Therefore, in addition to edgewise brackets and lightwire brackets, there have been developed combination brackets. Such combination brackets permit the use of either the edgewise technique or the lightwire technique using the same bracket. Examples of such combinations brackets are shown in U.S. Pat. Nos. 3,178,822 and 3,163,933. Although in/out compensation is provided in prior art combination brackets for the edgewise slot, in/out compensation has not heretofore been provided for both the edgewise slot and the lightwire slot.

Furthermore, because of the configuration of prior art orthodontic brackets, both an edgewise archwire and a lightwire archwire could not be attached to the bracket using a single fastening pin or a single fastening member. The use of multiple fastening members to attach both archwires is undesirable because they require additional labor to install those fastening members and they provide additional patient discomfort. Also, prior art combination brackets have heretofore been undesirably large causing difficulties in application and patient discomfort.

Therefore, a combination orthodontic bracket has long been sought which can be used for both edgewise and lightwire corrective techniques, which provides in/out compensation in both the edgewise slot and the lightwire slot, which requires only a single fastening member to attach both archwires to the bracket and which is relatively small and comfortable to wear.

SUMMARY OF THE INVENTION

The present invention satisfies the above-described needs by providing an improved orthodontic bracket. The improved orthodontic bracket of the present invention comprises a solid body member having a base surface adapted for attachment to a tooth, a labial surface, an occlusal side and a gingival side; a first slot formed in said body member extending transverse said body member intermediate said occlusal side and said gingival side opening at said labial surface and extending from said labial surface toward said base surface to a first distance from said base surface; a second slot formed in said gingival side of said body member extending transverse said body member intermediate said labial surface and said base surface, said second slot being located said first distance from said base surface; and a pin slot extending from said gingival side to said occlusal side of said body member transverse said first and second slots, said pin slot being located intermediate said labial surface and said base surface at a second distance from said base surface greater than said first distance and such that when a pin having an elongate body and a head at one end thereof is inserted in said pin slot, said body of said pin captures an archwire in said first slot and said head of said pin captures an archwire in said second slot thereby positioning both said archwires in said body member said first distance from said base surface of said body member.

In an alternate embodiment of the present invention the orthodontic bracket comprises a solid body member having a base surface adapted for attachment to a tooth, a labial surface, an occlusal side and a gingival side; a first slot formed in said body member extending transverse said body member intermediate said occlusal side and said gingival side opening at said labial surface and extending from said labial surface toward said base surface to a first distance from said base surface; a second slot formed in said gingival side of said body member extending transverse said body member intermediate said labial surface and said base surface, said second slot being located said first distance from said base surface; and a pin slot extending from said gingival side to said occlusal side of said body member transverse said first and second slots, said pin slot being located intermediate said labial surface and said base surface at a second distance from said base surface lesser than said first distance and such that when a pin having an elongate body and a head at one end thereof is inserted in said pin slot, said head of said pin captures an archwire in said second slot thereby positioning said archwire said first distance from said base surface of said body member.

Accordingly, it is an object of the present invention to provide an improved orthodontic bracket.

Another object of the present invention is to provide an orthodontic bracket which provides the same in/out compensation for both an edgewise slot and a lightwire slot.

A further object of the present invention is to provide an orthodontic bracket which is relatively small and comfortable to wear.

Still another object of the present invention is to provide an orthodontic bracket which can secure both an edgewise archwire and a lightwire archwire using a single fastening member.

Another object of the present invention is to provide an orthodontic bracket to which it is relatively easy to attach both an edgewise archwire and a lightwire archwire simultaneously.

Yet another object of the present invention is to provide an orthodontic bracket for use with a pin fastening member which prevents undesired rotation of the pin fastening member.

These and other objects, features and advantages of the present invention will become apparent after a review of the following detailed description of the disclosed embodiments and the appended drawing and claims.

DETAILED DESCRIPTION OF THE DISCLOSED EMBODIMENTS

Figure 1:
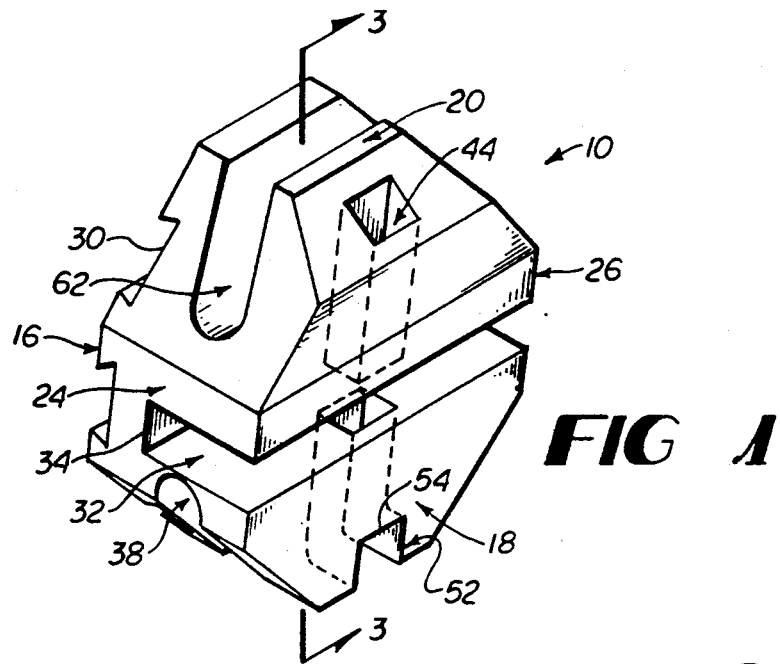
FIG. 1 is a perspective view of a disclosed embodiment of the improved orthodontic bracket of the present invention with a pin slot shown in phantom.
Figure 2:
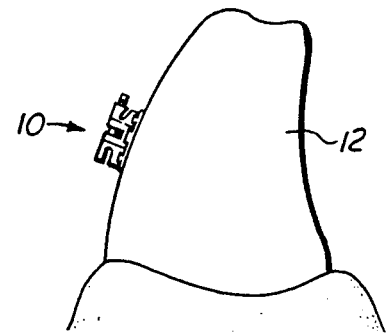
FIG. 2 is a side view of the improved orthodontic bracket shown in FIG. 1 attached to a tooth.

With reference to the drawing in which like numbers indicate like elements throughout the several views, it can be seen that there is an orthodontic bracket 10 for temporary attachment to a tooth 12 (FIG. 2) using well known conventional adhesive or cementing techniques. The particular method used to attach the bracket 10 to a tooth does not form a part of the present invention.

The bracket 10 is made from a solid piece of surgical stainless steel. The bracket 10, in the various configurations, as will be described below, can be made by machining a solid block of material, or, preferably, by casting using techniques well known in the art, such as the lost wax technique.

With reference to FIGS. 1 through 5, 10 and 11, there is shown a first embodiment of the present invention in which the bracket 10 comprises a body member 14 having a base surface 16, a labial surface 18, an occlusal surface 20, a gingival surface 22, a left surface 24 and a right surface 26. The base surface 16 includes a plurality of dovetail-shaped slots 30 formed therein. The base surface 16 is sized and shaped to be attached to the tooth 12. The dovetail-shaped slots 30 in the base surface 16 are provided so that the adhesive or cement which is used to attach the bracket 10 to the tooth 12 flows into the dovetail-shaped slots and more firmly anchors the bracket to the adhesive or cement.

The labial surface 18 of the body member 14 includes an edgewise slot 32 formed therein. The edgewise slot 32 has a rectangularly-shaped cross-section and extends from the labial surface 18 toward the base surface 16 and terminates a predetermined distance from the base surface. The bottom 34 of the edgewise slot 32 is therefore spaced from the base surface 16 a desired distance. The edgewise slot 32 is sized and shaped to receive an edgewise archwire 36.

The gingival surface 22 has a lightwire slot 38 formed therein. The lightwire slot 38 extends from the gingival surface 22 toward the occlusal surface 20 and terminates a predetermined distance from the edgewise slot 32. The lightwire slot 38 is sized and shaped to receive a lightwire archwire 40. The lightwire slot 38 includes shoulders 39a, 39b which slope toward the occlusal surface 74 from a central point in the lightwire slot outwardly toward the left surface 24 and the right surface 26. The sloping shoulders 39a, 39b permit the bracket 10 to freely tip about a lightwire archwire received in the lightwire slot 38.

The lightwire slot 38 includes a side wall 42 proximate the base surface 16. The lightwire slot 38 is positioned in the gingival surface 22 between the base surface 16 and the labial surface 18 so that the side wall 42 is located the same distance from the base surface 16 as the bottom 34 of the edgewise slot 32. When the edgewise archwire 36 and the lightwire archwire 40 are positioned in the edgewise slot 32 and the lightwire slot 38 respectively, the edgewise archwire and the lightwire archwire are both positioned the same distance from the base surface 16. It is this distance of the edgewise archwire 36 and lightwire archwire 40 from the base surface 16 which determines the compensation for in/out. Therefore, it can be seen that the bracket 10, shown for example in FIG. 4, has the same amount of in/out compensation for both the edgewise slot 32 and the lightwire slot 38.

Figure 4:
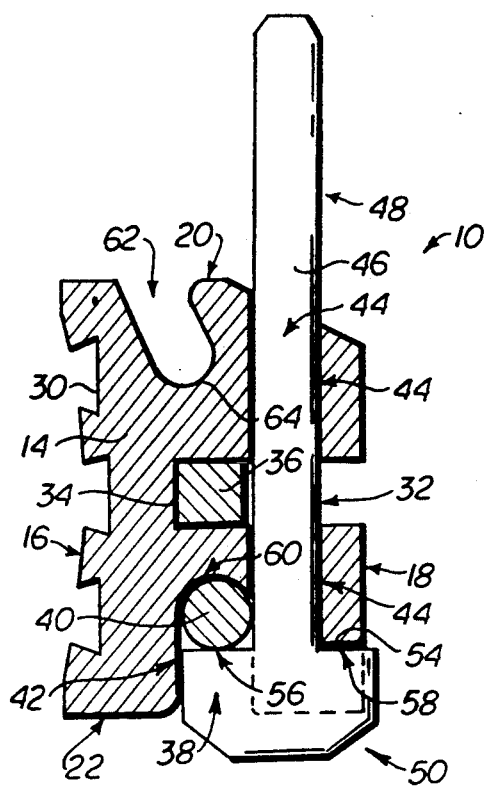
FIG. 4 is a cross-sectional view of the improved orthodontic bracket shown in FIG. 3 showing the attachment of both an edgewise archwire and a lightwire archwire with a single pin.
Figure 5:
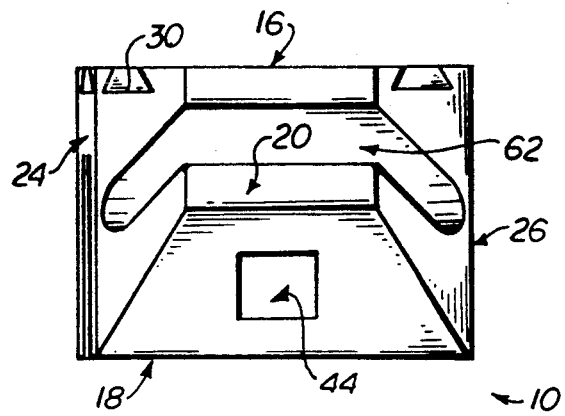
FIG. 5 is a top plan view of the improved orthodontic bracket shown in FIG. 1.
Figure 6:
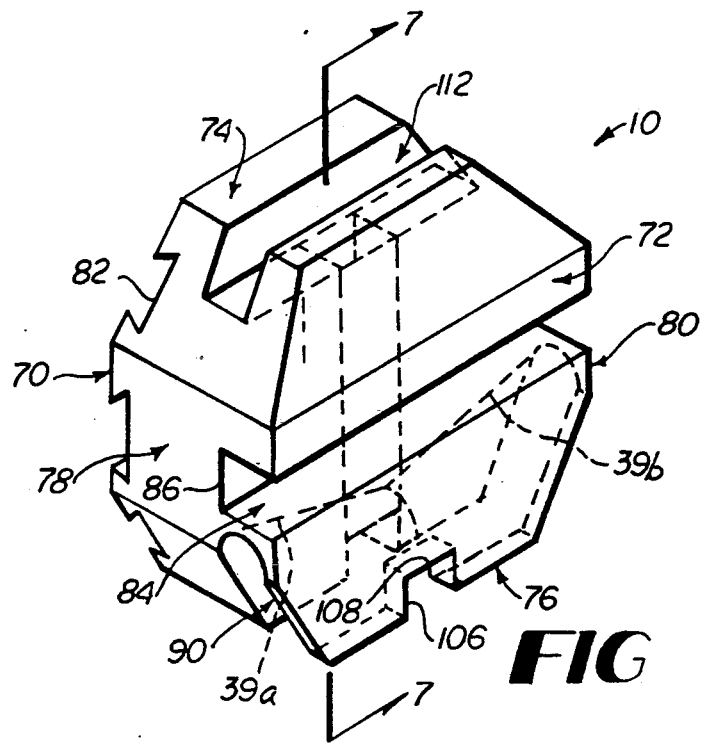
FIG. 6 is a perspective view of an alternate embodiment of the improved orthodontic bracket of the present invention with the pin slot, lightwire slot and retaining slot shown in phantom.

The body member 14 of the bracket 10 also includes a pin slot 44 which extends from the gingival surface 22 to the occlusal surface 20 intermediate the labial surface 18 and the lightwire slot 38 substantially parallel the labial surface and transverse the edgewise slot 32. The pin slot 44 is sized and shaped to receive a T-shaped retaining pin 46 having a elongate portion 48 and an enlarged head portion 50. The pin slot 44 is further positioned so that when the elongate portion 48 of the pin 46 is inserted in the pin slot 44, as shown in FIG. 4, the pin captures the edgewise archwire 36 between the pin and the body member 14 of the bracket 10 thereby retaining the archwire in the edgewise slot 32 adjacent the bottom 34 thereof.

The labial surface 18 has a notch 52 formed therein adjacent the gingival side surface 22. The notch 52 extends from the labial surface 18 to the lightwire slot 38. The notch 52 also extends from the gingival side surface 22 toward the occlusal surface 20 terminating at an end 54. The head portion 50 of the pin 46 includes shoulders 56, 58. When the pin 46 is inserted in the pin slot 44 such that the shoulder 58 of the head portion 50 of the pin abuts the end 54 of the notch 52, as shown in FIG. 4, the shoulder 56 of the head portion captures the lightwire archwire 40 in the lightwire slot 38 adjacent the end 60 thereof. The notch 52, in conjunction with the head 50 of the pin 46, also prevents rotation of the pin in the slot 44.

The occlusal side surface 20 optionally has a retaining slot 62 formed therein. The retaining slot 62 is located on the occlusal side surface 20 intermediate the base surface 16 and the pin slot 44. The retaining slot 62 extends from the occlusal side surface 20 toward the gingival side surface 22 at an angle toward the labial surface 18 and terminates at an end 64.

In order to use the bracket 10 of the present invention, the base surface 16 is adhered to the tooth 12 in the conventional manner using a well known adhesive or cement. With reference to FIG. 4, the archwire 36 is positioned in the edgewise slot 32 adjacent the bottom 34 thereof. The lightwire archwire 40 is then positioned in the lightwire slot 38 adjacent the end 60 thereof. The pin 46 is then inserted in the pin slot 44 so that the shoulder 58 abuts the end 54 of the notch 52. The free end of the elongate portion 48 of the pin 46 is then bent toward the right surface 26 so that the pin is retained in the pin slot.

As can be seen from the foregoing, when the bracket of the present invention is used in this configuration, both the edgewise archwire 36 and the lightwire archwire 40 are positioned the same distance from the bottom surface 16 of the body 14, thereby providing the same in/out compensation for both archwires. Furthermore, both the edgewise archwire 36 and the lightwire archwire 40 are retained in their respective slots 32, 38 by a single retaining member, i.e., the pin 46.

Figure 3:
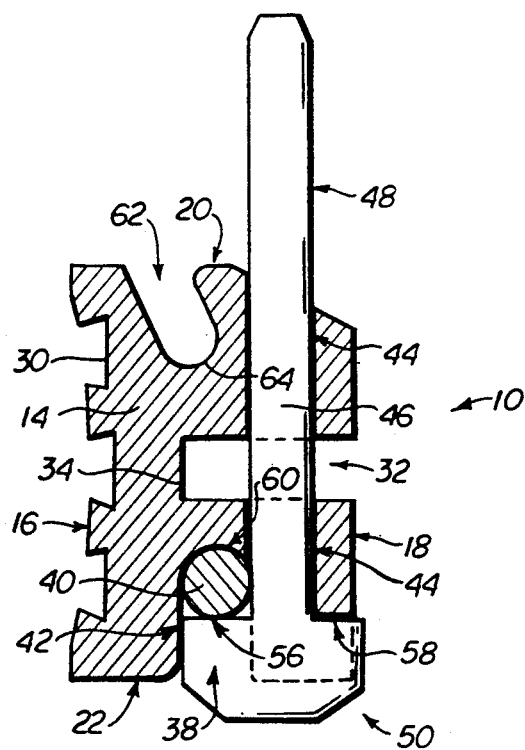
FIG. 3 is a cross-sectional view taken along the line 3—3 of the improved orthodontic bracket shown in FIG. 1 showing the attachment of a single lightwire archwire with a pin.

If it is desired to not use the pin 46 to hold the edgewise archwire 36 and the lightwire archwire 40 in place, a conventional tie wire (not shown), well known in the art, can be used by looping the tie wire through the retaining slot 62, over the labial surface 18 and through the lightwire slot 38. The same retaining system, i.e., either the pin 46, the donut retaining member or the tie wire, can be used to retain a single archwire 36 in the edgewise slot 32 or the pin 46 can be used to retain a single lightwire archwire 40 in the lightwire slot 38, as shown in FIG. 3.

With reference to FIGS. 6 through 9, 12 and 13, there is shown a second embodiment of the present invention in which the bracket 10 comprises a body member 68 having a base surface 70, a labial surface 72, an occlusal surface 74, a gingival surface 76, a left surface 78 and a right surface 80. The base surface 70 includes a plurality of dovetail-shaped slots 82 formed therein. The base surface 70 is sized and shaped to be attached to the tooth 12. The dovetail-shaped slots 82 in the base surface 70 are provided so that the adhesive or cement which is used to attach the bracket 10 to the tooth 12 flows into the dovetail-shaped slots and more firmly anchors the bracket to the adhesive or cement.

The labial surface 72 of the body member 68 includes an edgewise slot 84 formed therein. The edgewise slot 84 has a rectangularly-shaped cross-section and extends from the labial surface 72 toward the base surface 70 and terminates a predetermined distance from the base surface. The bottom 86 of the edgewise slot 84 is therefore spaced from the base surface 70 a desired distance. The edgewise slot 84 is sized and shaped to receive an edgewise archwire 88.

The gingival surface 76 has a lightwire slot 90 formed therein. The lightwire slot 90 extends from the gingival surface 76 toward the occlusal surface 74 and terminates a predetermined distance from the edgewise slot 84 at an end 92. The lightwire slot 90 is sized and shaped to receive a lightwire archwire 94.

The lightwire slot 90 includes a side wall 96 proximate the base surface 70. The lightwire slot 90 is positioned in the gingival surface 76 between the base surface 70 and the labial surface 72 so that the side wall 96 is located the same distance from the base surface 70 as the bottom 86 of the edgewise slot 84. When the edgewise archwire 88 and the lightwire archwire 94 are positioned in the edgewise slot 84 and the lightwire slot 90 respectively, the edgewise archwire and the lightwire archwire are both positioned the same distance from the base surface 70. It is this distance of the edgewise archwire 88 and lightwire archwire 94 from the base surface 70 which determines the compensation for in/out. Therefore, it can be seen that the bracket 10 shown in FIG. 8 has the same amount of in/out compensation for both the edgewise slot 84 and the lightwire slot 90.

The body member 68 of the bracket 10 also includes a pin slot 98 which extends from the gingival surface 76 to the occlusal surface 74 intermediate the bottom 86 of the edgewise slot 84 and the side wall 96 of the lightwire slot 90 and the base surface 70 substantially parallel to the base surface and transverse the edgewise slot. The pin slot 98 is sized and shaped to receive an L-shaped retaining pin 100 having an elongate portion 102 and a leg portion 104.

Figure 7:
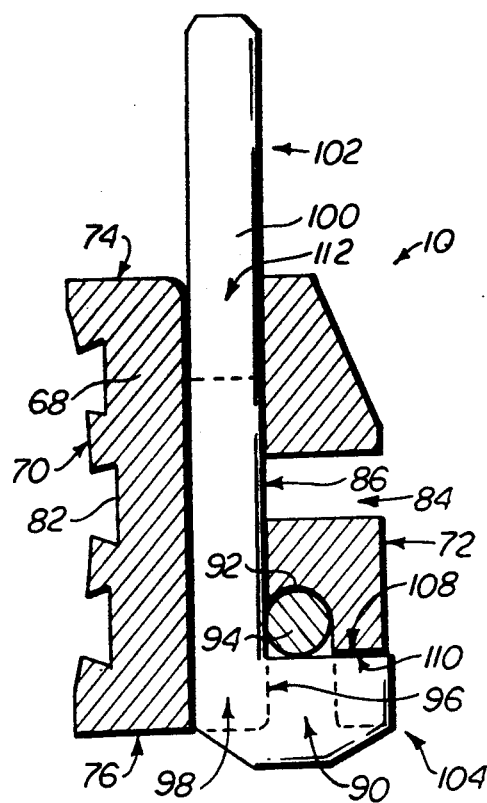
FIG. 7 is a cross-sectional view taken along the line 7—7 of the improved orthodontic bracket shown in FIG. 6 showing the attachment of a single lightwire archwire with a pin.

The labial surface 72 has a notch 106 formed therein adjacent the gingival side surface 76. The notch 106 extends from the labial surface 72 to the lightwire slot 90. The notch 106 also extends from the gingival side surface 76 toward the occlusal surface 74 terminating at an end 108. The leg portion 104 of the pin 100 includes a shoulder 110. When the pin 100 is inserted in the pin slot 98 such that the shoulder 110 of the leg portion 104 of the pin abuts the end 108 of the notch 106, as shown in FIG. 7, the shoulder of the leg portion captures the lightwire archwire 100 in the lightwire slot 90 adjacent the end 92 thereof. The notch 106, in conjunction with the leg portion 104 of the pin 100, prevents rotation of the pin in the slot 98.

The occlusal side surface 74 has a retaining slot 112 formed therein. The retaining slot 112 is located on the occlusal side surface 74 intermediate the base surface 70 and the labial surface 72 and coplanar with the pin slot 98. The retaining slot 112 extends from the left side surface 78 to the right side surface 80.

Figure 8:
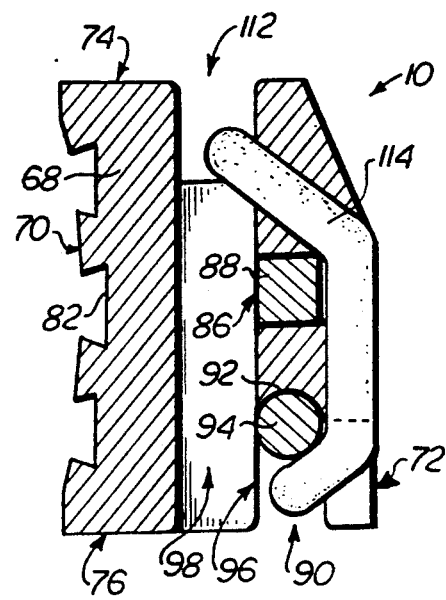
FIG. 8 is a cross-sectional view of the improved orthodontic bracket shown in FIG. 7 showing the attachment of both an edgewise archwire and a lightwire with a tie wire.
Figure 9:
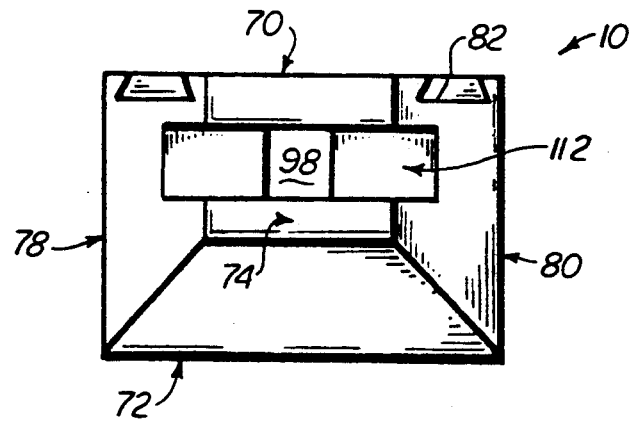
FIG. 9 is an top plan view of the improved orthodontic bracket shown in FIG. 6.
Figure 10:
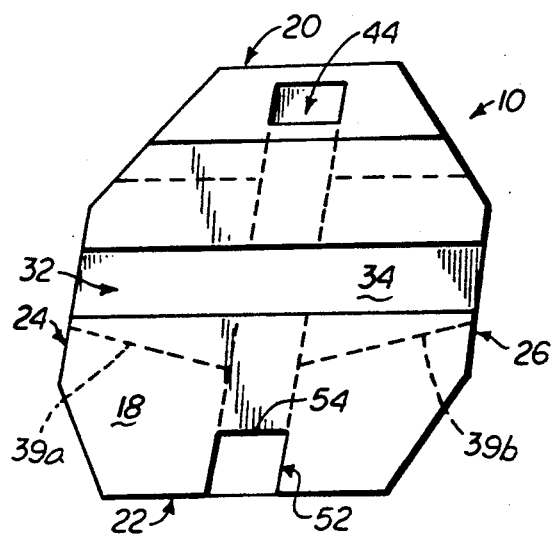
FIG. 10 is a labial view of the improved orthdontic bracket shown in FIG. 1 with the pin slot, lightwire slot and retaining slot shown in phantom.
Figure 11:
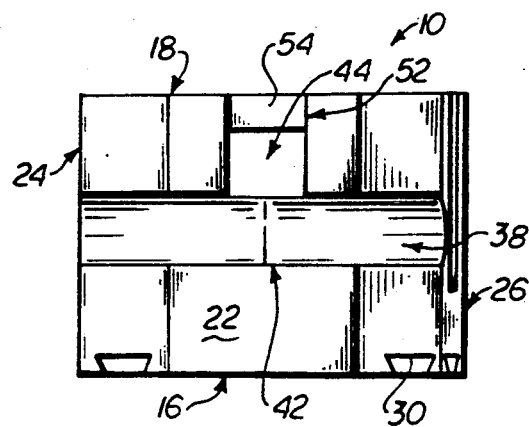
FIG. 11 is a bottom plan view of the improved orthodontic bracket shown in FIG. 6.
Figure 12:
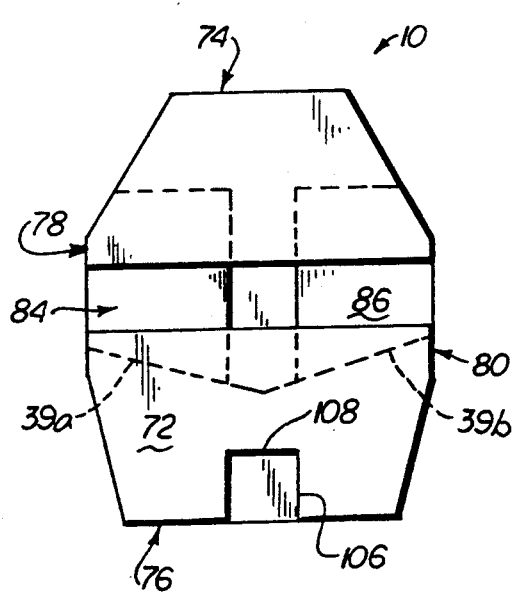
FIG. 12 is a labial view of the improved orthodontic bracket shown in FIG. 6 with the pin slot, lightwire slot and retaining slot shown in phantom.
Figure 13:
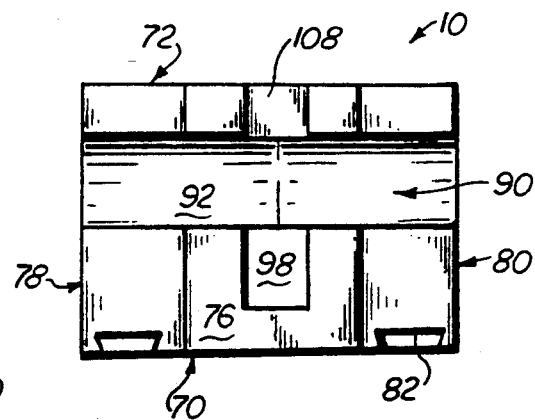
FIG. 13 is a bottom plan view of the improved orthodontic bracket shown in FIG. 6.

In order to use the bracket 10 of the present invention, the base surface 70 is adhered to the tooth 12 in the conventional manner using a well known adhesive or cement. With reference to FIG. 8, the archwire 88 is positioned in the edgewise slot 84 adjacent the bottom 86 thereof. The lightwire archwire 94 is then positioned in the lightwire slot 90 adjacent the end 92 thereof. A tie wire 114 is then inserted in the retaining slot 112 passed over the labial surface 72 and inserted into the lightwire slot 90, as shown in FIG. 8.

As can be seen from the foregoing, when the bracket of the present invention is used in this configuration, both the edgewise archwire 88 and the lightwire archwire 94 are positioned the same distance from the bottom surface 70 of the body 68, thereby providing the same in/out compensation for both archwires. Furthermore, both the edgewise archwire 88 and the lightwire archwire 94 are retained in their respective slots 84, 90 by a single retaining member.

If it is desired, as shown in FIG. 7, the pin 100 can be used to retain a single lightwire archwire 94 in the lightwire slot 90. The lightwire archwire 94 is positioned in the lightwire slot 90 adjacent the end 92 thereof. The elongate portion 102 of the pin 100 is then inserted in the pin slot 112 so that the shoulder 110 of the leg portion 104 abuts the end 108 of the notch 106. The free end of the elongate portion 102 of the pin 100 is then bent toward either the left side 78 or the right side 80 to thereby secure the pin in the pin slot 98. As can be seen, the lightwire archwire 94 is captured in the lightwire slot 90 between the end 92 of the lightwire slot and the shoulder 110 of the pin 100 and retained thereby.

It should be understood, of course, that the foregoing relates only to certain disclosed embodiments of the present invention and that numerous modifications or alterations may be made therein without departing from the spirit and scope of the invention as set forth in the appended claims.

What is claimed is:

1. A combination orthodontic bracket for simultaneous use with both lightwire and edgewise corrective techniques comprising:

a body member having a base surface adapted for attachment to a tooth, a labial surface, an occlusal side and a gingival side;

a first slot for receiving an archwire, said first slot being formed in said body member extending transverse said body member intermediate said occlusal side and said gingival side opening at said labial surface and extending from said labial surface toward said base surface to a first distance from said base surface, said first slot being sized and shaped for use in the edgewise corrective technique;

a second slot for receiving an archwire, said second slot being formed in said gingival side of said body member extending transverse said body member intermediate said labial surface and said base surface, said second slot being located said first distance from said base surface, said second slot being sized and shaped for use in the lightwire corrective technique, said second slot including sloped shoulders to permit tipping of said bracket when a lightwire archwire is received in said second slot; and a pin slot extending from said gingival side to said occlusal side of said body member transverse said first and second slots, said pin slot being located intermediate said slots and said base surface such that when a pin having an elongate body and an enlarged head at one end thereof is inserted in said pin slot, said enlarged head of said pin can capture a lightwire archwire in said second slot thereby retaining said lightwire archwire in said second slot and positioning said lightwire archwire said first distance from said base surface of said body member.

2. The orthodontic bracket of claim 1 further comprising a third slot formed in said occlusal side of said body member extending transverse said body member intermediate said base surface and said labial surface, said second and third slots being sized and shaped to receive an O-shaped retaining member to thereby capture both an archwire in said first slot and an archwire in said second slot when a pin is not inserted in said pin slot and said retaining member is engaged in said second and third slots thereby positioning both said archwires in said body member said first distance from said base surface of said body member.

3. A combination orthodontic bracket for simultaneous use with both lightwire and edgewise corrective techniques comprising:
   a body member having a base surface adapted for attachment to a tooth, a labial surface, an occlusal side and a gingival side;
   a first slot for receiving an archwire, said first slot being formed in said body member extending transverse said body member intermediate said occlusal side and said gingival side opening at said labial surface and extending from said labial surface toward said base surface to a first distance from said base surface, said first slot being sized and shaped for use in the edgewise corrective technique;
   a second slot for receiving an archwire, said second slot being formed in said gingival side of said body member extending transverse said body member intermediate said labial surface and said base surface, said second slot being located said first distance from said base surface, said second slot being sized and shaped for use in the lightwire corrective technique, said second slot including sloped shoulders to permit tipping of said bracket when a lightwire archwire is received in said second slot; and
   a pin slot extending from said gingival side to said occlusal side of said body member transverse said first and second slots, said pin slot being located intermediate said labial surface and said base surface at a second distance from said base surface greater than said first distance and such that when a pin having an elongate body and a head at one end thereof is inserted in said pin slot, said body of said pin can capture an archwire in said first slot and said head of said pin can capture a lightwire archwire in said second slot thereby positioning both said archwire and said lightwire archwire in said body member said first distance from said base surface of said body member.

4. The orthodontic bracket of claim 3 further comprising a third slot formed in said occlusal side of said body member extending transverse said body member intermediate said base surface and said pin slot, said second and third slots being sized and shaped to receive an O-shaped retaining member to thereby capture an archwire in said second slot when a pin is not inserted in said pin slot and said retaining member is engaged in said second and third slots.

5. In a combination orthodontic apparatus for simultaneous use in the application of lightwire and edgewise corrective techniques and including a solid metal bracket body member, archwire, lightwire archwire, and a locking pin to fasten said archwire and/or said lightwire archwire to said bracket in the application of said edgewise technique and/or said lightwire technique, the improvement comprising said bracket body member having:
   a base surface for attachment to a tooth, a labial surface, an occlusal side surface and a gingival side surface;
   a first slot for receiving an archwire, said first slot being formed in said body member extending transverse said bracket body member intermediate said occlusal side surface and said gingival side surface opening at said labial surface and extending from said labial surface toward said base surface to a first distance from said base surface, said first slot being sized and shaped to receive an archwire in the portion of said first slot adjacent said base surface so that said archwire is positioned said first distance from said base surface, said first slot being sized and shaped for use in the edgewise corrective technique;
   a second slot for receiving an archwire, said second slot being formed in said gingival side surface of said body member extending transverse said body member intermediate said labial surface and said base surface, said second slot being located said first distance from said base surface so that said lightwire archwire is positioned said first distance from said base surface, said second slot being sized and shaped for use in the lightwire corrective technique, said second slot including sloped shoulders to permit tipping of said bracket when a lightwire archwire is received in said second slot;
   a pin slot extending from said gingival side surface to said occlusal side surface of said body member transverse said first and second slots, said pin slot being located intermediate said labial surface and said base surface at a second distance from said base surface greater than said first distance and such that when said pin is inserted in said pin slot, said pin captures said archwire in said first slot and said lightwire archwire in said second slot thereby positioning both said archwire and said lightwire archwire in said body member said first distance from said base surface of said body member; and
   a third slot formed in said occlusal side surface of said body member extending transverse said body member intermediate said base surface and said pin slot, said second and third slots being sized and shaped to receive a retaining member to thereby capture a lightwire archwire in said second slot when a pin is not inserted in said pin slot and said retaining member is engaged in said second and third slots.

* * * * *